United States Patent
Goldmann et al.

(10) Patent No.: US 8,790,389 B2
(45) Date of Patent: Jul. 29, 2014

(54) TUBULAR COLORED VESSEL PROSTHESIS AND USE THEREOF IN SURGERY

(75) Inventors: Helmut Goldmann, Tuttlingen/Donau (DE); Hartmut Rimpler, Berlin (DE)

(73) Assignee: Aesculap AG (DE)

( * ) Notice: Subject to any disclaimer, the term of this patent is extended or adjusted under 35 U.S.C. 154(b) by 789 days.

(21) Appl. No.: 12/280,806

(22) PCT Filed: Mar. 2, 2007

(86) PCT No.: PCT/EP2007/001794
§ 371 (c)(1), (2), (4) Date: Oct. 16, 2008

(87) PCT Pub. No.: WO2007/101613
PCT Pub. Date: Sep. 13, 2007

(65) Prior Publication Data
US 2010/0030323 A1 Feb. 4, 2010

(30) Foreign Application Priority Data
Mar. 3, 2006 (DE) .......................... 10 2006 011 218

(51) Int. Cl.
*A61F 2/06* (2013.01)
(52) U.S. Cl.
USPC ........................................................ 623/1.34
(58) Field of Classification Search
USPC ............... 623/1.39, 1.44, 1.46, 1.45, 1.34; 600/36; 427/2.1, 2.25; 606/8, 153, 155
See application file for complete search history.

(56) References Cited

U.S. PATENT DOCUMENTS

| | | | |
|---|---|---|---|
| 3,805,301 A | 4/1974 | Liebig | |
| 5,990,379 A * | 11/1999 | Gregory | 128/898 |
| 6,197,050 B1 * | 3/2001 | Eno et al. | 623/1.36 |
| 6,306,176 B1 * | 10/2001 | Whitbourne | 623/23.59 |
| 6,462,169 B1 | 10/2002 | Shalaby | |
| 6,794,485 B2 | 9/2004 | Shalaby et al. | |
| 7,052,512 B2 * | 5/2006 | Yang et al. | 623/1.46 |
| 7,638,156 B1 * | 12/2009 | Hossainy et al. | 427/2.1 |
| 2002/0120326 A1 * | 8/2002 | Michal | 623/1.15 |
| 2003/0018353 A1 | 1/2003 | Yang et al. | |
| 2003/0047126 A1 * | 3/2003 | Tomaschko | 116/201 |
| 2004/0024448 A1 * | 2/2004 | Chang et al. | 623/1.42 |
| 2004/0109892 A1 | 6/2004 | Shalaby | |
| 2004/0253185 A1 | 12/2004 | Herweck et al. | |
| 2005/0060021 A1 * | 3/2005 | O'Brien et al. | 623/1.15 |

FOREIGN PATENT DOCUMENTS

| | | |
|---|---|---|
| DE | 695 33 806 | 12/2005 |
| EP | 1 016 422 A1 | 7/2000 |
| FR | 2 866 239 | 8/2005 |
| WO | 90/14810 | 12/1990 |
| WO | 94/06373 | 3/1994 |
| WO | 00/10488 | 3/2000 |
| WO | 02/094133 | 11/2002 |
| WO | 2005/027794 | 3/2005 |

* cited by examiner

*Primary Examiner* — David Isabella
*Assistant Examiner* — Jacqueline Woznicki
(74) *Attorney, Agent, or Firm* — DLA Piper LLP (US)

(57) ABSTRACT

A tubular vessel prosthesis includes an inner surface and an outer surface and a wall, where the vessel prosthesis has a coloration on the inner and/or outer surface which brings about a contrast between the inner surface and outer surface.

17 Claims, 2 Drawing Sheets

TUBULAR COLORED VESSEL PROSTHESIS AND USE THEREOF IN SURGERY

RELATED APPLICATIONS

This is a §371 of International Application No. PCT/EP2007/001794, with an international filing date of Mar. 2, 2007 (WO 2007/101613 A2, published Sep. 13, 2007), which is based on German Patent Application No. 102006011218.0, filed Mar. 3, 2006.

TECHNICAL FIELD

This disclosure relates to a tubular colored vessel prosthesis, and use thereof in surgery.

BACKGROUND

The vessel prostheses normally employed in surgical management are white or black in color. In the particular case of textile vessel prostheses, the white-colored appearance is produced and/or enhanced by so-called "white pigments," for example, titanium dioxide. The black coloration of vessel prostheses is frequently produced by a coating with pyrolytic carbon. Besides these, gray and brown colored vessel prostheses are also employed, and their colors are attributable in particular to appropriate silver salt coatings.

A disadvantage of known colored vessel prostheses is that three-dimensional identifiability by the surgeon is in some cases only moderate, for example, in the context of endoscopic operations and checks. Further disadvantages may derive from a suboptimal suture adjustment with non-uniform stitch lengths and distances, whereby it is possible for the risks of inadequate anchoring of the prosthesis at the implantation site to be increased.

It could therefore be advantageous to provide a colored vessel prosthesis which improves identifiability by the surgeon compared with known vessel prostheses and allows manipulation (handling) intended to be as simple and uncomplicated as possible.

SUMMARY

We provide a tubular vessel prosthesis having an inner surface, an outer surface and a wall, wherein coloration on the inner and/or outer surface brings about a contrast between the inner and outer surfaces.

We also provide a method of replacing at least a portion of a blood vessel including fixing opposed ends of the vessel prosthesis to open ends of one or more blood vessels in a patient.

We further provide a method of bridging over at least a portion of a blood vessel in a patient including inserting the vessel prosthesis into at least a portion of the blood vessel.

DETAILED DESCRIPTION

Figure 1:
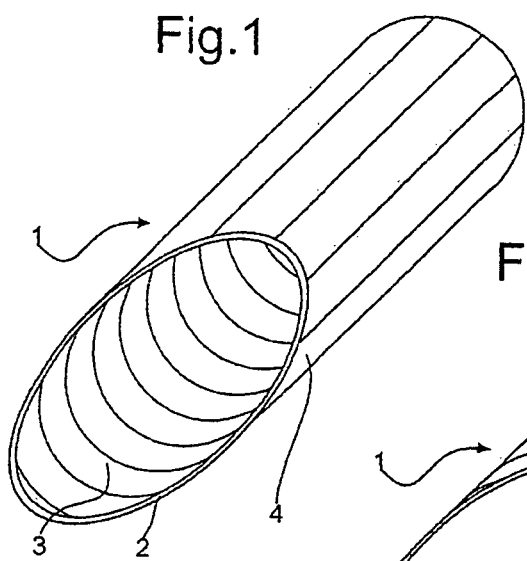
FIG. 1 shows a perspective view of a vessel prosthesis.

I provide a tubular vessel prosthesis with an inner surface and an outer surface and a wall, where the vessel prosthesis has a coloration on the inner and/or outer surface which brings about a contrast between the inner surface and outer surface. The effect thereof is an improved three-dimensional identifiability which makes it easy for the surgeon to apply satisfactory sutures. This is particularly advantageous for obliquely cut vessel prostheses because the inner surface is particularly clearly visible in this case.

In one aspect, the coloration is two-dimensional and extends on at least one part of the inner and/or outer surface of the vessel prosthesis. The coloration of the vessel prosthesis is preferably a so-called "continuous coloration." A continuous coloration as used herein is intended to mean coloration which extends substantially without interruption on the entire inner and/or outer surface of the vessel prosthesis.

In a further aspect, the coloration of the vessel prosthesis is opaque. Opaque means that the prosthesis material present under the coloration is not visible to the user.

In a particularly preferred aspect of the vessel prosthesis, the coloration is sealing. A "sealing coloration" is intended to mean a coloration which makes the vessel prosthesis impermeable, especially for fluids, for example, body fluids. The loss of body fluid, preferably of blood, on implantation of the vessel prosthesis can advantageously be avoided through the sealing, preferably absorbable, coloration of the vessel prosthesis.

The coloration of the vessel prosthesis is particularly advantageously caused by a colored coating or by a colored impregnation, preferably by a colored impregnation. The coating or impregnation of the vessel prosthesis may comprise at least one biological material, for example collagen, gelatin and/or albumin. In a preferred aspect of the vessel prosthesis, the coating or impregnation comprises at least one polymer, at least one copolymer, preferably at least one terpolymer. The polymer may be a star polymer which can preferably be prepared in the presence of a tri- or tetrafunctional organic compound and in the: presence of an organometallic catalyst. The tri- or tetrafunctional compound may be at least one of glycerol, ethanetrimethylol, propanetrimethylol, pentaerythritol or triethanolamine. Such star polymers are disclosed in U.S. Pat. No. 6,462,169 B1, the entire contents of which are incorporated herein by reference.

It is particularly advantageous for the coating or impregnation to comprise a synthetic absorbable polymer. In a particularly preferred aspect of the vessel prosthesis, the coating or impregnation comprises a polymer based on glycolide, lactide, ε-caprolactone and/or trimethylene carbonate.

In a further aspect of the vessel prosthesis, the coloration has a luminous color. This may increase the contrast between the inner and outer surfaces of the vessel prosthesis and thus improve its manipulation, preferably in relation to its three-dimensional identifiability, on implantation. It is further preferably provided for the coloration of the vessel prosthesis to be non-reflective. The non-reflecting properties of the vessel prosthesis allow suture adjustment on ligation of the vessel prosthesis with natural vessel organs, preferably with blood vessels, to be secure and accurate.

In a particularly preferred aspect, the vessel prosthesis is multicolored, preferably bicolored.

In a further particularly preferred aspect of the vessel prosthesis, the inner and outer surfaces each have a coloration, with the inner surface of the vessel prosthesis having a coloration different from the outer surface. It is provided for the coloration differences between the inner and outer surfaces of the vessel prosthesis to derive from different, especially very different, coloration intensities of the same color. The different coloration between the inner and outer surfaces can be ascribed to a particular extent to the fact that the dyes responsible for the coloration, especially the colored coating or the colored impregnation, do not penetrate completely through the wall into the interior of the vessel prosthesis.

Concerning further properties of the dyes, reference is made to the following description. A contrast between the inner and outer surfaces of the vessel prosthesis is generated particularly advantageously in this way and leads to an improvement in the three-dimensional appearance of the vessel prosthesis. It is impossible through the improved contrast visualization between the inner and outer surfaces of the vessel prosthesis to identify better, and where appropriate correct, faults in implantation of the vessel prosthesis, for example, a non-uniform suture adjustment.

A further possibility is for the vessel prosthesis to be colored at the ends of the inner and/or outer surface, preferably at the ends of the outer surface. It is advantageous for the vessel prosthesis to have different colorations at its ends. The vessel prosthesis may where appropriate have further colorations between its colored prosthesis ends. The colorations are preferably configured as colored rings which are disposed at uniform distances on the inner and/or outer surface, preferably on the outer surface, of the vessel prosthesis. It is thus possible, for example, for different diameters in the vessel prosthesis, which may be in conical form, to be visualized better.

In a particularly preferred aspect, the vessel prosthesis is uncolored (white) on the inner surface and colored on the outer surface. This may have the effect in an advantageous manner of enhancing the contrast between the inner surface and outer surface of the vessel prosthesis.

The coloration of the vessel prosthesis is preferably caused by biocompatible dyes. The dyes maybe dyes for suture materials, in particular dyes for absorbable suture materials.

In one aspect of the vessel prosthesis, the coloration is attributable to water-soluble dyes, in particular to food coloring agents. Such dyes are particularly suitable for coating or impregnating compositions on an aqueous basis.

In a particularly preferred aspect, the coloration of the vessel prosthesis is caused by at least one dye which is soluble in organic solvents such as in ketones. Such dyes are particularly suitable for coating or impregnating compositions based on polymer-based coating or impregnating compositions soluble in organic solvents. The organic solvents are preferably 3-pentanone and/or acetone, with preference for 3-pentanone. It is particularly preferred for the dye which is soluble in organic solvents to be D & C (Drug & Cosmetic) No. 2 and/or D & C (Drug & Cosmetic) No. 6.

The coloration of the vessel prosthesis may furthermore be caused by a plurality of dyes, in particular by a dye mixture.

It is particularly preferred for the coloration of the vessel prosthesis to derive from at least one bright color different from red. This is particularly advantageous because a contrast to the red color of human and/or animal blood is produced in this way, thus making it possible to avoid faults, for example, through inaccurate suture adjustments. This makes it possible, overall for manipulation of the vessel prosthesis by the surgeon to be distinctly facilitated.

In an advantageous aspect of the vessel prosthesis, the coloration comprises at least one color selected from the group of violet, blue, green and yellow. It is particularly preferred for the outer surface of the vessel prosthesis to have a blue to violet coloration. The outer surface of the vessel prosthesis preferably has a blue to violet coloration, and the inner surface has a paler blue to violet coloration. In a further preferred aspect, the outer surface of the vessel prosthesis has a blue to violet coloration and the inner surface is uncolored.

In another preferred aspect, the outer surface of the vessel prosthesis has a green coloration. The outer surface of the vessel prosthesis preferably has a green coloration, and the inner surface has a paler green coloration. It is particularly preferred for the outer surface of the vessel prosthesis to have a green coloration and for the inner surface to be uncolored.

The vessel prosthesis preferably has a textile construction. The vessel prosthesis is advantageously a knitted or woven vessel prosthesis. The vessel prosthesis can be produced by specific knitting or weaving techniques. The knitting, and weaving techniques are generally known so that a more detailed description is not needed.

The vessel prosthesis may further be configured as a so-called "nonwoven structure," preferably of expanded polytetrafluoroethylene (ePTFE) or polyurethane. The vessel prosthesis is preferably a nonwoven structure, preferably a spray-bonded nonwoven structure, in particular made of polyurethane.

The vessel prosthesis is preferably formed from multifilament yarn. Multifilament vessel prostheses have, because of the capillary forces occurring between the individual filaments, an optimal uptake capacity for fluids, in particular for body fluids, preferably for blood. This may be particularly advantageous in the case of non-impregnated vessel prostheses for sealing through blood clotting during the implantation.

The wall materials of the vessel prosthesis may be at least one of polypropylene, polyester, for example, polyethylene terephthalate (PET), expanded polytetrafluoroethylene (ePTFE) or polyurethane. Polyurethane, especially linear polyurethane, preferably linear aliphatic polyurethane, is particularly suitable, because of its high elasticity and especially low material-related thrombogenicity, as wall material for the vessel prosthesis.

I further provide a process for producing the vessel prosthesis, comprising the step:
    application of at least one colored solution or of at least one colored suspension to a vessel prosthesis or to wall materials of the vessel prosthesis.

In a preferred aspect of the process, the ends of the vessel prosthesis are tightly closed before application, of the colored solution or colored suspension. It is possible in this way particularly advantageously to produce a vessel prosthesis which has a contrast between the inner and outer surfaces. Depending on the impermeability of the closure, and the prosthesis wall it is possible to produce a vessel prosthesis whose inner surface is uncolored or whose inner surface has a coloration different from that of the outer surface of the vessel prosthesis. The materials for the closure of the prosthesis ends and for the prosthesis wall are preferably chosen so that, after coloring, the vessel prosthesis has an inner surface which has a coloration different from that of the outer surface of the vessel prosthesis. The closure materials and wall materials preferably used prevent the colored solution or colored suspension passing completely through the sealing of the prosthesis ends and through the wall of the vessel prosthesis. A preimpregnation, especially of the inner surface, with colorless or differently colored impregnating compositions may be advantageous.

In a particularly preferred aspect of the process, the open ends of the vessel prosthesis are tightly closed for coloration. It is possible in this way to advantageously produce the different colorations between the inner and outer surfaces of the vessel prosthesis. Concerning further details thereof, reference is made to the previous description.

In a further aspect of the process, a colored coating solution or colored impregnating solution is applied to the vessel prosthesis. In another aspect, a colored coating suspension or colored impregnating suspension is applied to the vessel prosthesis.

It is further possible for the colored solution or colored suspension to be applied to a previously impregnated or coated vessel prosthesis, in which case the vessel prosthesis preferably has a colorless coating or impregnation.

It is particularly advantageous to employ colored collagen, gelatin or albumin suspensions for the coloration of the vessel prosthesis and/or the wall materials, thereof. As an alternative thereto it is advantageously possible to use colored solutions of polymers in organic solvents. The organic solvents preferably used are ketones, preferably 3-pentanone and/or acetone. The color of the polymer solutions is particularly advantageously achieved by adding dyes which are soluble in organic solvents, preferably D & C (Drug & Cosmetic) No. 2 and/or D & C (Drug & Cosmetic) No. 6. It is particularly advantageous for colored polymer solutions composed of bioabsorbable polymers to be used, in which case preferably copolymer solutions, advantageously terpolymer solutions, especially tetrapolymers, based on glycolide, lactide, ϵ-caprolactone and/or trimethylene carbonate are employed for coloration. For further details, reference is made to the previous description.

In a preferred aspect of the process, application of the colored solution or colored suspension is carried out by spraying.

In another especially preferred aspect of the process, application of the colored solution or colored suspension is carried out by immersing the vessel prosthesis and/or the wall materials thereof in the colored solution or colored suspension. It is likewise possible for the colored solution or colored suspension to be poured over the vessel prosthesis.

In a further aspect of the process, the colored solution or colored suspension is forced from the inside through the prosthesis wall, preferably by exerting pressure. This procedure is particularly preferred for the coloring of prostheses having a nonwoven structure. In the case of coloration of the vessel prosthesis with a colored polymer solution or suspension, the inner wall of the vessel prosthesis can be rinsed with organic solvents such as ketones, preferably with 3-pentanone and/or acetone, to remove the colored polymers adhering to the inner wall after coloring the vessel prosthesis.

In another particularly preferred aspect of the process, the dyes are incorporated into the polymers. The dyes are preferably added to a polymer melt. The colored polymer melt is preferably granulated after cooling and with preference added to uncolored granules.

In the case of prostheses composed of sprayed layers, for example, of a spray-bonded nonwoven, sequential use of differently colored polymer solutions is possible. A structure composed of differently colored layers is obtained in this way.

To produce the vessel prosthesis it is possible to provide for application to an uncolored or colored vessel prosthesis, in which case an uncolored vessel prosthesis is preferably used for the application.

A further possibility is to produce textile vessel prostheses by using two differently colored thread systems, in which case one thread system, preferably composed of white threads, is preferably located on the inside of the vessel prosthesis, and the other thread system, preferably composed of colored threads, is on the outside of the vessel prosthesis.

Finally, I provide for the use of the vessel prosthesis to replace or bridge over blood vessels. Concerning further details, reference is made to the above description.

The vessel prosthesis is distinguished from known vessel prostheses by a distinctly improved contrast between the inner and outer surfaces. The three-dimensional identifiability by the surgeon is distinctly improved thereby. The distinctly improved contrast of the vessel prosthesis compared with the prior art has the effect of accurate and preferably uniform suture adjustment. This is particularly important in relation to the ligation of the vessel prosthesis to natural vessel organs, preferably blood vessels.

An obliquely cut vessel prosthesis 1 is shown in FIG. 1 and has a wall 2 with an inner surface 3 which has a coloration differing from that of the outer surface 4. The different colorations of the vessel prosthesis are made apparent by the different patterns of lines which depict the inner surface 3 and outer surface 4 of the vessel prosthesis 1.

Figure 2:
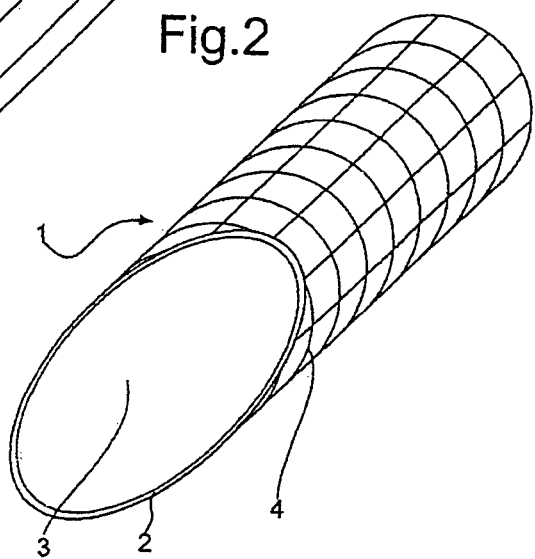
FIG. 2 shows a perspective view of another prosthesis.

An obliquely cut vessel prosthesis 1 is shown in FIG. 2 and has a wall 2 which is uncolored on the inner surface 3 and has a blue-violet coloration on the outer surface 4. The blue-violet coloration of the outer surface 4 of the vessel prosthesis 1 is made apparent by a pattern of lines running substantially perpendicularly.

Figure 3:
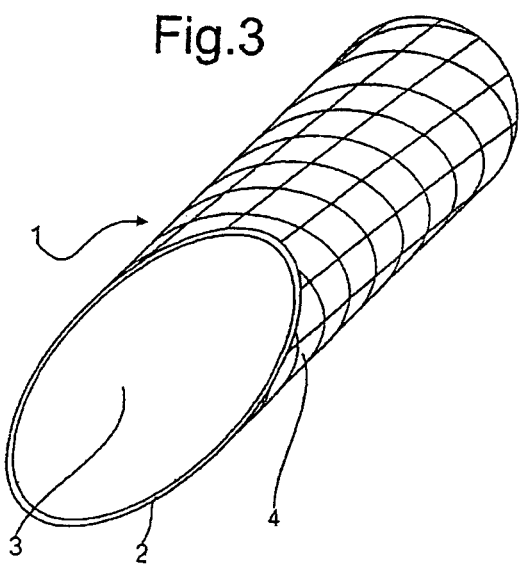
FIG. 3 shows a perspective view of yet another prosthesis.

An obliquely cut vessel prosthesis 1 is shown in FIG. 3 and has a wall 2 which is uncolored on the inner surface 3 and has a green coloration on the outer surface 4. The green coloration on the outer surface 4 of the vessel prosthesis 1 is made apparent by a pattern of lines running substantially rhomboidally.

Figure 4:
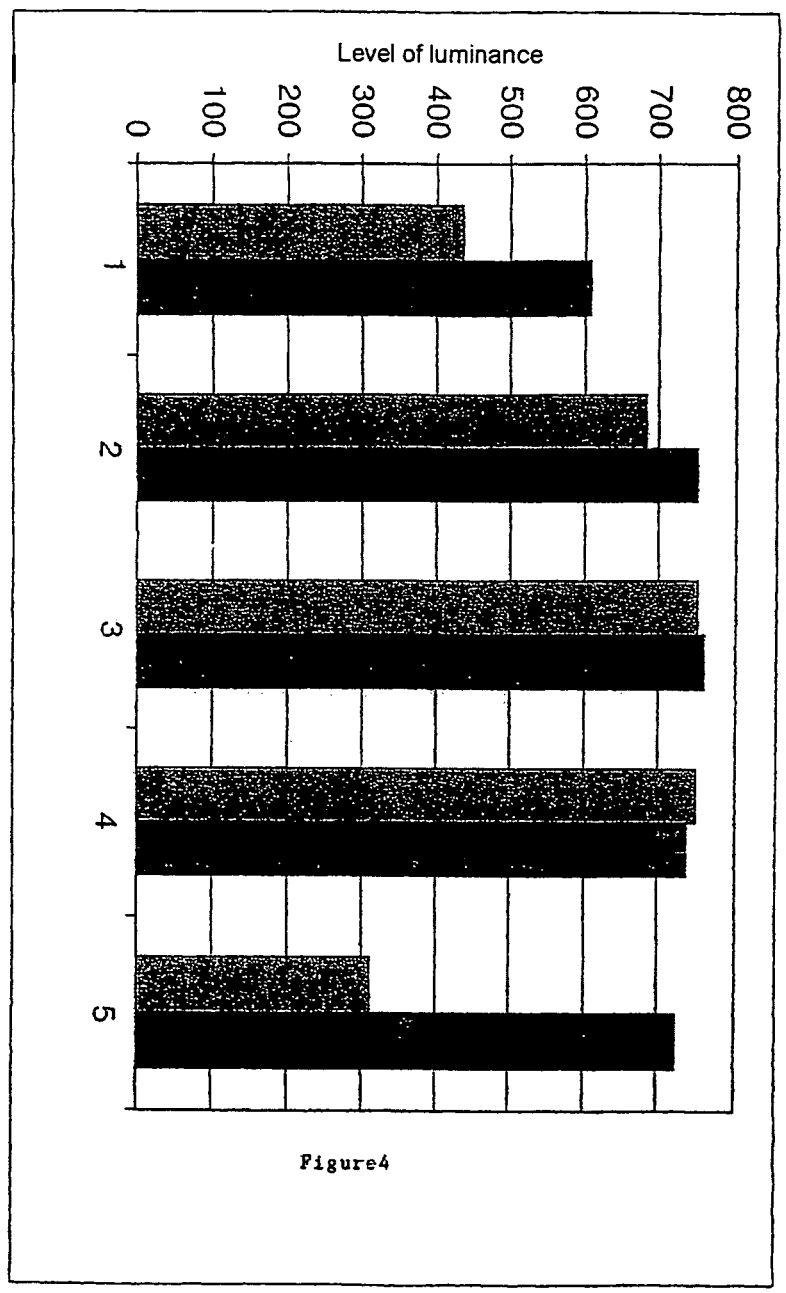
FIG. 4 shows a histogram of contrast measurements taken from selected vessel prostheses.

The results of the contrast measurement of various vessel prostheses are shown graphically in FIG. 4 in the form of a histogram. The level of the luminance [mV] is indicated on the ordinate of the graph. Various measured vessel prostheses 1 to 5 are indicated on the abscissa. The pale bars reflect in each case the measured level of luminance on the outer surface of the particular vessel prosthesis. The dark bars reflect in each case the measured level of luminance on the inner surface of the particular vessel prosthesis. Vessel prosthesis 1 is a vessel prosthesis colored with silver acetate; Vessel prosthesis 2 is a silver-coated vessel prosthesis. Vessel prosthesis 3 is an uncoated colorless vessel prosthesis. Vessel prosthesis 4 is a vessel prosthesis with an uncolored coating. Vessel prostheses 1 to 4 just mentioned and identified are known. By contrast, vessel prosthesis 5 is a vessel prosthesis colored and polymer-coated and having a blue coloration on the outer surface and having a distinctly paler blue coloration or being colorless on the inner surface. The contrast for the particular vessel prostheses is derived from the difference of the measured levels of luminance on the inner surface and outer surface of the particular vessel prostheses.

Further features and details are evident from the following description of an example. In this connection, the individual features can in each case be implemented on their own or in combinations of a plurality with one another. The example serves merely as an illustrative guide, which is not intended in any way to be restricted thereto.

EXAMPLE

Production of a Colored Nonwoven Vessel Prosthesis

The prosthesis wall is produced by spraying a solution of linear polyurethane in chloroform onto a rotating bar. Subsequently, a polymer solution colored with D & C violet No. 2 is applied, likewise by spraying, onto the sprayed polyurethane layer. A nonwoven vessel prosthesis which has a violet coloration on its outer surface, whereas its inner surface has a distinctly paler violet coloration compared with the outer surface, or is uncolored, is obtained in this way.

Production of a Colored and Knitted Vessel Prosthesis

A vessel prosthesis knitted from polyethylene terephthalate (PET) is coated with a gelatin suspension in a known manner. In this case, the vessel prostheses are drawn onto metal rods, whose diameter and shape are appropriate for the particular prosthesis, before the coating process and are fixed at the ends; for example, with cable binder. The gelatin suspension comprises a water-soluble blue dye which is responsible for a coloration of the vessel prosthesis in accordance with Example 1 (very different intensities of coloration of the same color on the inner surface and outer surface of the vessel prosthesis). The gelatin can subsequently be crosslinked with diisocyanate and treated further in a usual way.

Production of a Colored and Knitted Vessel Prosthesis Using Two Thread Systems

A two-bed warp knitting machine and a white and blue thread system are used to produce the vessel prosthesis. The warp knitting machine is adjusted so that the white threads are mainly located on the inside of the knit and the blue threads mainly on the outside of the knit. The small proportion of blue threads visible on the inside of the knit means that the produced vessel prosthesis has only a slight coloration on the inside, so that there is a large difference in the intensity of coloration of the same color compared with the outside of the vessel prosthesis. It is likewise possible in this way to achieve an unambiguous difference in contrast between the inner surface and outer surface of the vessel prosthesis.

Contrast Measurement of Vessel Prostheses

The contrast of the following vessel prostheses was determined during the current measurement series:
1. Vessel prosthesis 1
2. Vessel prosthesis 2
3. Vessel prosthesis 3
4. Vessel prosthesis 4
5. Vessel prosthesis 5

The contrast of vessel prostheses 1 to 5 was measured using a 180 W xenon light source with connected endoscopy camera with 1-CCD (charged coupled devices) and a so-called vector-scope. The contrast was measured by means of the level [mV] of luminance (image brightness or intensity). For calibration, this optical test arrangement with connected endoscopy camera and connected illumination was pointed at a white area. The illumination intensity of the xenon light source was adjusted so that a luminance level of 760 mV was reached.

To measure the contrast, vessel prostheses 1 to 5 were placed in each case on a black area. The xenon light source with connected endoscopy camera was then pointed in each case at the vessel prosthesis.

Contrast measurement of the vessel prostheses led to the following measured results:

| Sample | Outside | Inside |
| --- | --- | --- |
| Vessel prosthesis 1 | 434 | 608 |
| Vessel prosthesis 2 | 684 | 751 |
| Vessel prosthesis 3 | 751 | 760 |
| Vessel prosthesis 4 | 750 | 739 |
| Vessel prosthesis 5 | 311 | 725 |

Result:

The measured results clearly show that vessel prosthesis 5 shows a distinctly improved contrast between the inner and outer surfaces compared with the known vessel prostheses.

The invention claimed is:

1. A tubular vessel prosthesis having an inner surface, an outer surface and a wall,
    wherein the inner surface has a coloration different from a coloration of the outer surface and the coloration on the inner and outer surfaces brings about a contrast between the inner and outer surfaces,
    wherein the coloration on the inner and outer surfaces derives from at least one bright color different from red, the bright color comprising at least one color selected from the group consisting of violet, blue, green and yellow, and
    wherein the coloration on the inner and outer surfaces is attributable to dyes selected from the group consisting of water-soluble dyes and dyes soluble in organic solvents, and the coloration on both the inner and outer surfaces is attributable to the dyes.

2. The vessel prosthesis as claimed in claim 1, wherein the coloration is two-dimensional.

3. The vessel prosthesis as claimed in claim 1, having a coloration which extends without interruption on the entire inner and/or outer surface of the vessel prosthesis.

4. The vessel prosthesis as claimed in claim 1, wherein the coloration is sealing.

5. The vessel prosthesis as claimed in claim 1, wherein the coloration is a colored coating or colored impregnation.

6. The vessel prosthesis as claimed in claim 5, wherein the coating or impregnation comprises a synthetic absorbable polymer.

7. The vessel prosthesis as claimed in claim 1, wherein the coloration is non-reflective.

8. The vessel prosthesis as claimed in claim 1, which is multicolored.

9. The vessel prosthesis as claimed in claim 1, wherein the coloration is caused by at least one dye which is soluble in organic solvents.

10. The vessel prosthesis as claimed in claim 1, wherein the outer surface has a blue to violet coloration.

11. The vessel prosthesis as claimed in claim 1, wherein the outer surface has a green coloration.

12. The vessel prosthesis as claimed in claim 5, wherein the coating or impregnation comprises a synthetic absorbable polymer based on glycolide, lactide, $\epsilon$-caprolactone and/or trimethylene carbonate.

13. The vessel prosthesis as claimed in claim 1, which is bicolored.

14. The vessel prosthesis as claimed in claim 1, wherein the coloration is caused by at least one dye which is soluble in ketones.

15. A method of replacing at least a portion of a blood vessel comprising fixing opposed ends of the vessel prosthesis of claim 1 to open ends of one or more blood vessels in a patient.

16. A method of bridging over at least a portion of a blood vessel in a patient comprising inserting the vessel prosthesis of claim 1 into at least a portion of the blood vessel.

17. The vessel prosthesis of claim 1, wherein the wall is at least one selected from the group consisting of polypropylene, polyester, polyurethene, and polytetrafluoroethylene.

* * * * *